US00PP36377P2

(12) United States Plant Patent
Hansoti

(10) Patent No.: US PP36,377 P2
(45) Date of Patent: Jan. 7, 2025

(54) ***SANSEVIERIA* PLANT NAMED 'HANSOTI40'**

(50) Latin Name: *Sansevieria trifasciata*
Varietal Denomination: HANSOTI40

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 18/426,467

(22) Filed: Jan. 30, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./382
CPC ..... A01H 5/12; A01H 5/00; A01H 6/12
See application file for complete search history.

(56) References Cited

U.S. PATENT DOCUMENTS

PP33,126 P3 * 6/2021 Hansoti ..... A01H 6/12
Plt./382

* cited by examiner

*Primary Examiner* — June Hwu

(57) ABSTRACT

A new and distinct cultivar of *Sansevieria* plant named 'HANSOTI40' is disclosed, characterized by foliage having a vivid and distinct central broad band of longitudinal lighter golden yellow/greenish yellow streaks along length of the leaf lamina between the creamy yellow borders on both side of the leaf. This is combined with the transverse banding typical of most *Sansevieria trifasciata* cultivars but in this case this banding is more vivid because it is overlaid by the bright bands. Both combine to give the whole rosette an extra-bright look not seen in other cultivars of the Hahnii type. Rosettes are stiff and uniform. Plants require little water, having a moderate tolerance for drought, and are also tolerant of very wet conditions. The new variety is a *Sansevieria,* typically produced as an indoor ornamental plant.

7 Drawing Sheets

Latin name of the genus and species: *Sansevieria trifasciata.*

Variety denomination: 'HANSOTI40'.

BACKGROUND OF THE INVENTION

The present invention relates to a new and distinct cultivar of *Sansevieria* plant, botanically known as *Sansevieria trifasciata,* of the family Asparagaceae, hereinafter referred to by the cultivar name 'HANSOTI40'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI40' was discovered and selected by the inventor, Ashish Hansoti, as a single aberrant side shoot within a planting of *Sansevieria trifasciata* 'Hahnii Jade Marginata', a non-patented "Hahnii" or "Birds Nest" type of *Sansevieria* grown at a nursery in Village Vangani, District Thane, Maharashtra State in Western India. 'Hansoti 40' originated as a naturally-occurring mutation of the *Sansevieria trifasciata* variety 'Hahnii Jade Marginata', unpatented, in April 2018. The discovery was made in an outdoor container area.

Asexual reproduction of the new *Sansevieria* cultivar by vegetative cuttings was first performed in early 2019 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI40', which in combination distinguish this *Sansevieria* as a new and distinct cultivar:

1. Vivid and distinct central broad band of longitudinal lighter golden yellow/greenish yellow streaks along length of the leaf lamina between the creamy yellow borders on both side of the leaf.
2. This is combined with the transverse banding typical of most *Sansevieria trifasciata* cultivars but in this case this banding is more vivid because it is overlaid by the above bright bands. Both combine to give the whole rosette an extra-bright look not seen in other cultivars of the Hahnii type.
3. Another way to describe the rosette of 'HANSOTI40' is to say it's just like *Sansevieria trifasciata* 'Hahnii Jade Marginata', but with the additional central band of bright yellowish green, and a more vivid crossbanding giving an overall extra-bright appearance to the whole rosette.

Leaf width is quite variable and the strongest, healthiest plants have the widest leaves—this is true across all *Sansevieria trifasciata* cultivars known to the inventor. This variation means leaf width can be anything from 5 cm to 7 cm wide depending on season, growing conditions and plant vigour and plant age. Typically, the leaves are of medium width (6 cm average measured at the widest part of the mature leaf under good growing conditions) and lanceolate with a firm, waxy texture. The blades are thick and fleshy.

The new variety 'HANSOTI40' is a variety of *Sansevieria* in the group denominated as "Birds Nest" or 'Hahnii' types based on its origin. The new variety presents an average of 11 full size, mature leaves per plant when it reaches its saleable size (about 3 months from rooted cutting) but over time it can grow and accumulate many more leaves and increase in overall height.

The new variety is moderately drought tolerant and adapts well to conditions of bright light or heavy shade (exterior and interior). The intensity of these central bands varies with exposure to light and the contrast is most intense under higher light conditions. The plant is liable to get scorched in full hot sun.

The leaves show a variegated colouration, with a central wide area of darker green with typical *Sansevieria trifasciata* cross hatching and a border of lighter creamy yellow. This central darker green area along with the cross hatching is marked by a distinct longitudinal band consisting of lighter creamy green streaks, which is the major new and unusual feature of 'HANSOTI40'.

Each leaf has a marginal creamy yellow band similar to RHS Yellow 4B and varies in width from just 1 mm to 12 mm. This creamy yellow border is occasionally invaded with streaks of darker green from the central dark green area. This characteristic is seen in and is also seen in its parental cultivar, *Sansevieria trifasciata* 'Hahnii Jade Marginata'.

The central broad dark green area shows colouration similar to RHS Green 139A. There are the usual transverse horizontal bands on the leaves (typically seen in most *Sansevieria trifasciata* cultivars). The characteristic (and unique also to 'Hansoti 22' and the new 'HANSOTI40') golden yellow to greenish yellow streaks are between Yellow-Green N144C to N144D.

The backside of the leaves has similar coloration to the front except that the typical *Sansevieria trifasciata* transverse horizontal banding is more distinct. The central broad longitudinal band is very muted but is still seen on the back of the leaves.

Attached colour pictures are a better guide to the overall colouration and pattern than written descriptions. The primary distinctive characteristic is the lighter longitudinal band consisting of light golden yellow to greenish yellow streaks within the broad darker green central area.

PARENTAL COMPARISON

Plants of the new *Sansevieria* 'HANSOTI40' are similar to plants of the parental cultivar, however, 'HANSOTI40' differs in the characteristics described in Table 1.

TABLE 1

| | Characteristic | Parent Cultivar 'Hahnii Jade Marginata' | New cultivar 'Hansoti40' |
|---|---|---|---|
| 1. | Leaf size | 9 to 13 cm long | 9 to 13 cm long |
| 2. | Number of leaves | 9 to 12 leaves | 10 to 13 leaves |
| 3. | Variegation Pattern | Cream border on dark green leaves with typical *S. trifasciata* transverse banding. | Cream border on dark green leaves with typical *S. trifasciata* transverse banding plus a wide central band of light green/creamy yellow streaks |
| 4. | Border variegation | 2 to 12 mm | 1 to 12 mm wide |
| 5. | Central Variegation | Basic green background with distinct Transverse banding of light cream as seen in most *S. trifasciata* cultivars. | 20 to 30 mm wide band of lighter green/creamy yellow streaks on top of and in addition to the transverse banding. |

COMMERCIAL COMPARATOR

Plants of the new *Sansevieria* 'HANSOTI40' are similar to the commercial variety *Sansevieria* 'Hansoti22', U.S. Plant Pat. No. 33,126. Plants of the new *Sansevieria* 'HANSOTI40' differ from plants of the commercial cultivar 'Hansoti22' in the characteristics described in Table 2.

TABLE 2

| | Characteristic | Similar Cultivar 'Hansoti22' U.S. Plant Pat. No. 33126 | New cv 'Hansoti40' |
|---|---|---|---|
| 1. | Leaf size | 9 to 13 cm long | 9 to 13 cm long |
| 2. | Number of leaves | 9 to 12 leaves | 10 to 13 leaves |
| 3. | Variegation Pattern | Typical *S. trifasciata* 'Hahnii Jade Marginata' with added bright central band along length of leaf. Transverse banding essentially not seen. | Typical *S. trifasciata* 'Hahnii Jade Marginata' with added bright central band along length of leaf. Transverse banding is prominent. |
| 4. | Border variegation | 2 to 12 mm wide creamy band with inconspicuous transverse banding. | 1 to 9 mm wide creamy band with inconspicuous transverse banding. |
| 5. | Central Variegation | Only the Central bands of creamy streaks seen on dark green background with no transverse banding in leaf central area. | Lighter, brighter and more prominent transverse banding AND 20 to 30 mm wide band of lighter green/creamy yellow streaks |

BRIEF DESCRIPTION OF THE PHOTOGRAPHS

The accompanying photographs illustrate the overall appearance of the new *Sansevieria* cultivar 'HANSOTI40' showing the colors as true as is reasonably possible with colored reproductions of this type. Colors in the photographs may differ slightly from the color value cited in the detailed botanical description which accurately describe the color of 'HANSOTI40'.

These pictures illustrate the plant form which is the unique characteristic of 'HANSOTI40' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India. Various views of plants have been used.

Figure 1:
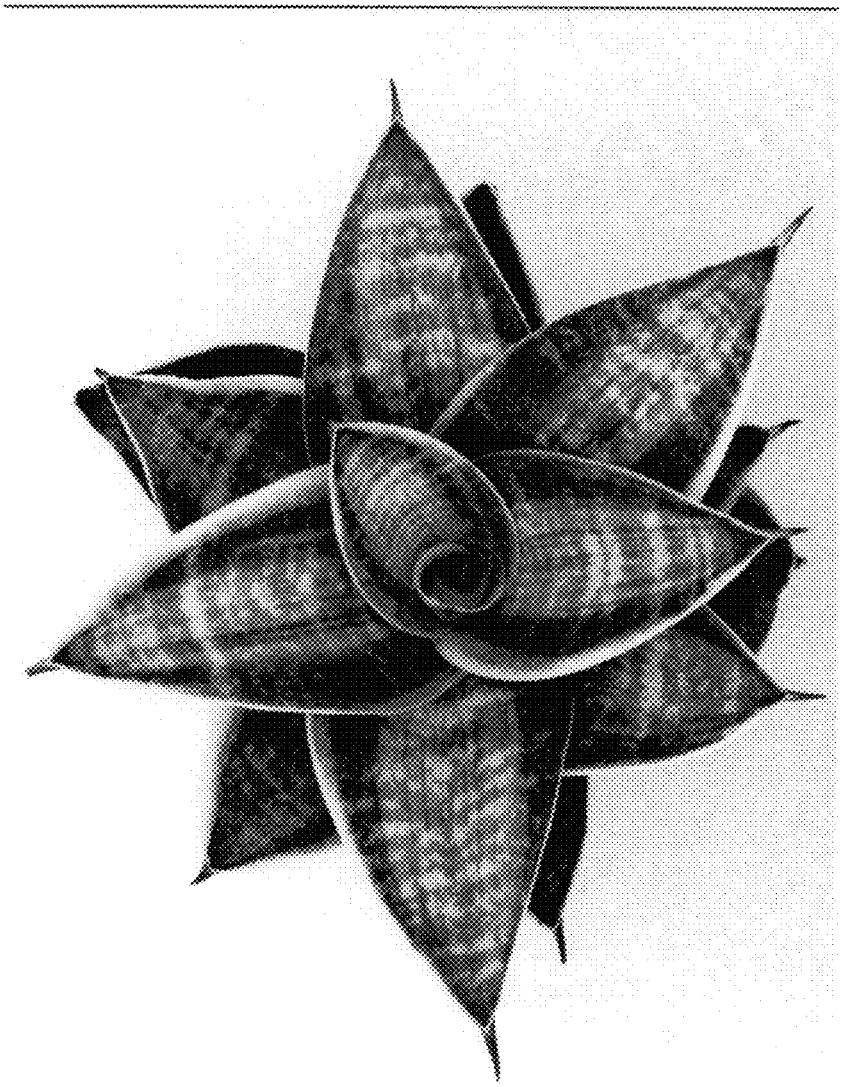
FIG. 1 depicts a three-month-old plant of *Sansevieria* 'HANSOTI40' in a 12 cm diameter pot.
Figure 2:
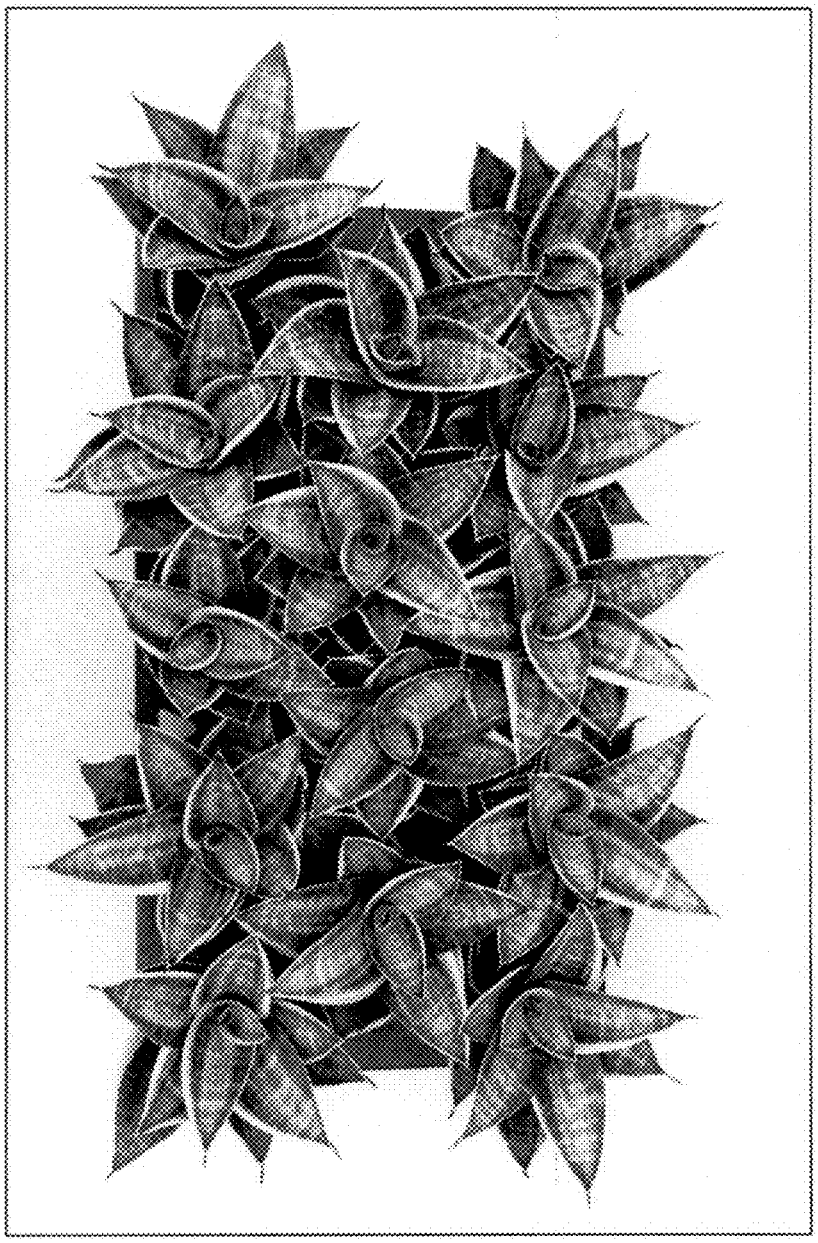
FIG. 2 shows a tray holding 14 'HANSOTI40' plants in 12 cm pots showing uniformity across multiple plants of this new cultivar.
Figure 3:
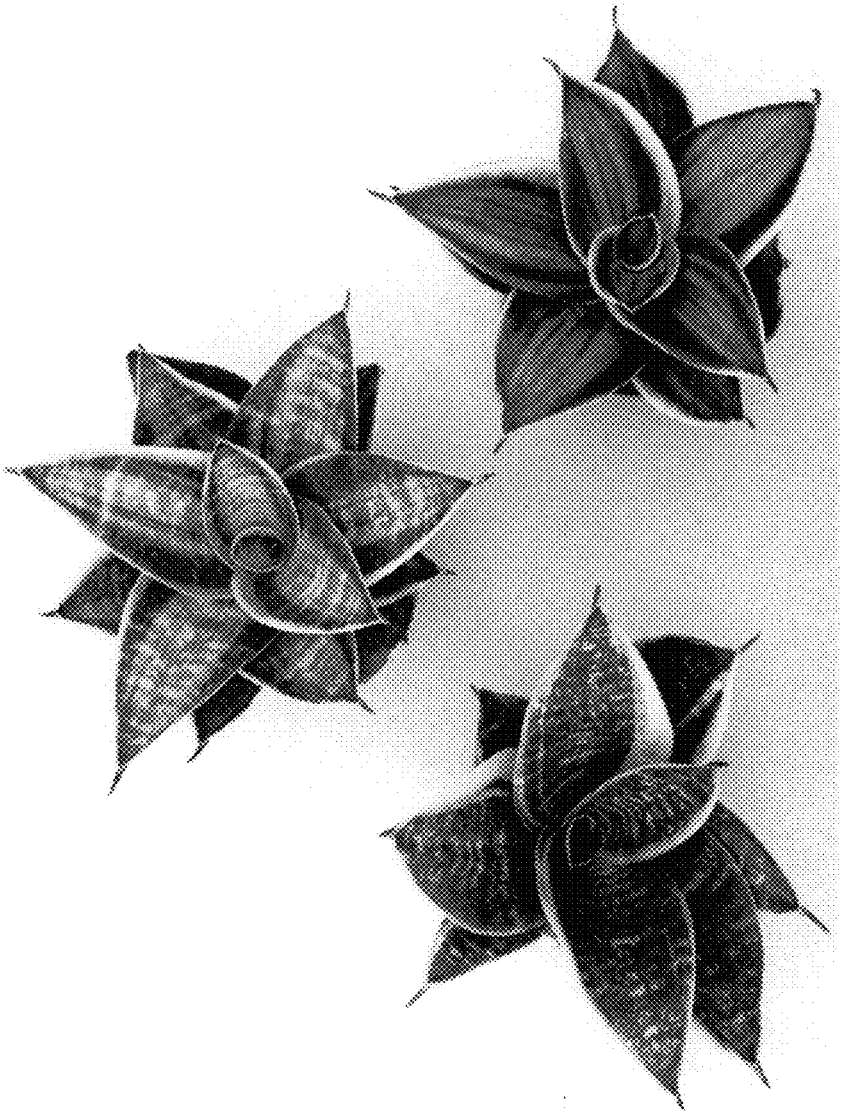

FIG. 3. is a comparison of the new cultivar, parent variety and a comparator cultivar from a top view. *Sansevieria trifasciata* 'Hahnii Jade Marginata', parental variety (bottom left) and *Sansevieria* 'Hansoti22' (bottom right) both compared with the new cultivar, *Sansevieria trifasciata* 'Hansoti40' (top).

Figure 4:
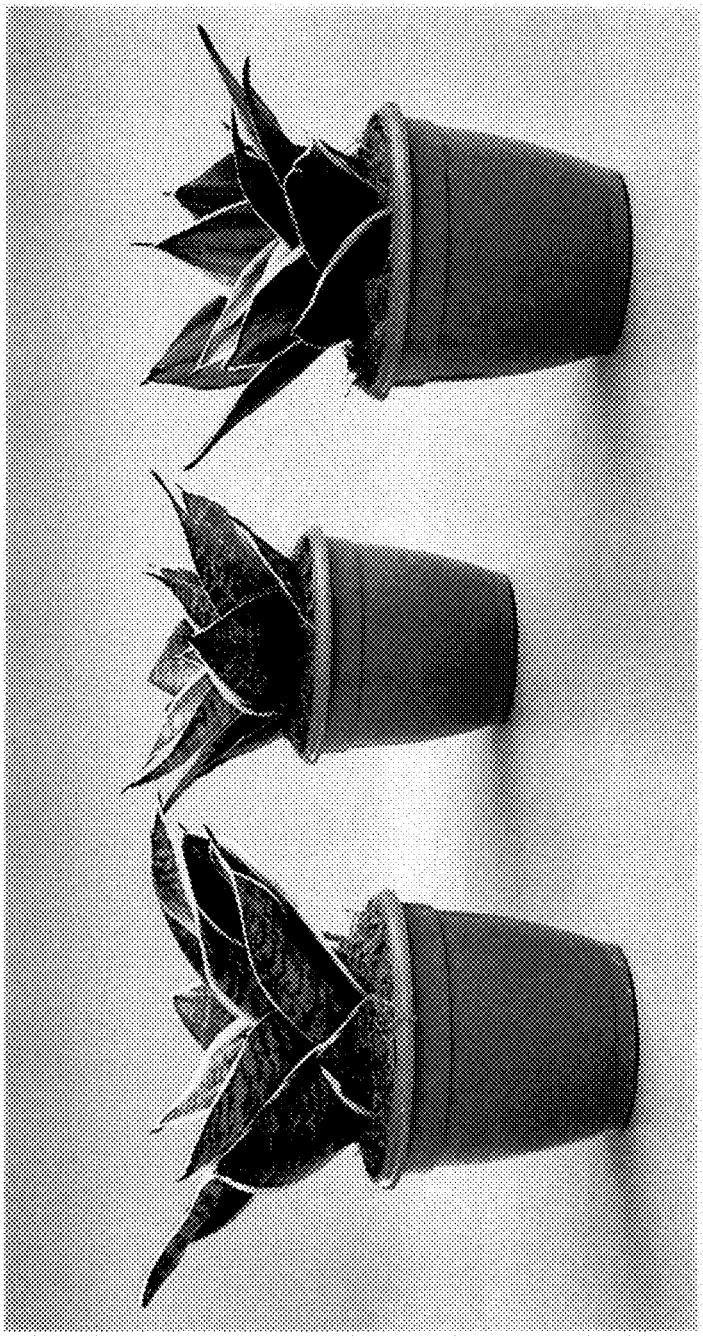

FIG. 4 is a comparison of the new cultivar, parent variety and a comparator cultivar from a sideview. *Sansevieria trifasciata* 'Hahnii Jade Marginata' the parental variety (left) and *Sansevieria* 'Hansoti22' (right) both compared with the new cultivar, *Sansevieria trifasciata* 'Hansoti40' (center).

Figure 5:
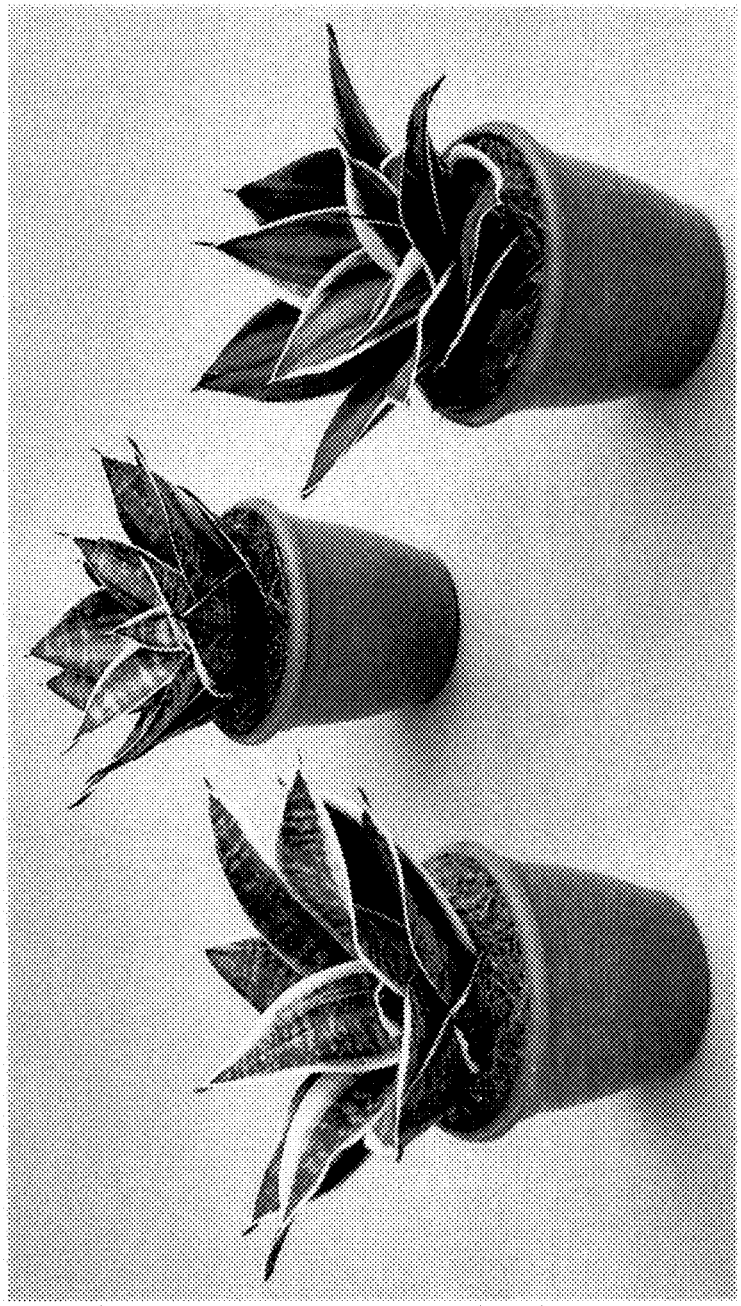

FIG. 5 is a comparison of the new cultivar, parent variety and a comparator cultivar from an upper-sideview. *Sansevieria trifasciata* 'Hahnii Jade Marginata', parental variety (left) and *Sansevieria* 'Hansoti22' (right) both compared with the new cultivar, *Sansevieria trifasciata* 'Hansoti40' (center).

Figure 6:
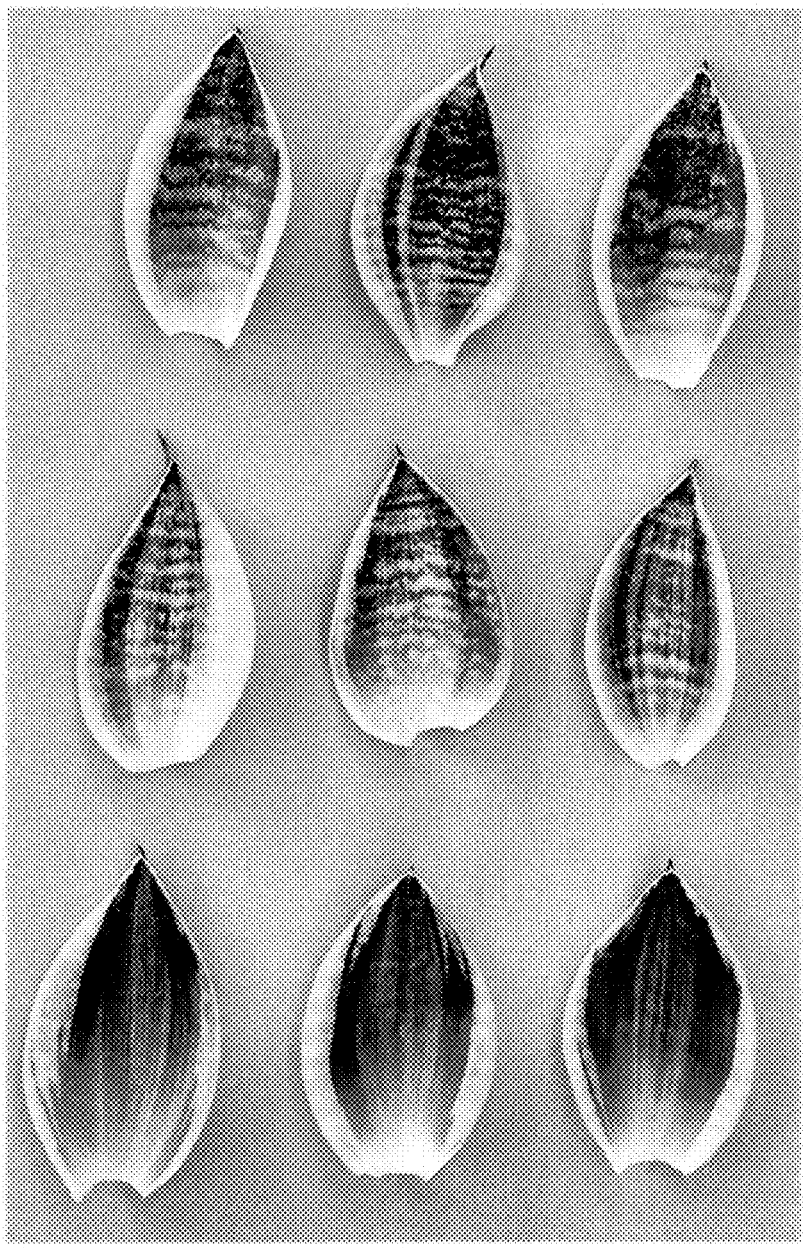

FIG. 6 is a comparison of the top surface foliage of the new cultivar, parent variety and a comparator cultivar. Individual leaves (top surface of leaves) of *Sansevieria trifasciata* 'Hahnii Jade Marginata', parental variety (Top row) and leaves of comparable variety *Sansevieria* 'Hansoti22' (Bottom row) and leaves of the new variety, *Sansevieria trifasciata* 'Hansoti40' (Middle row). It's very easy to see that the new variety, Hansoti40, is very similar to *Sansevieria trifasciata* 'Hahnii Jade Marginata' BUT with the addition of a band of cream lines running along the centre of the leaf along its length.

Figure 7:
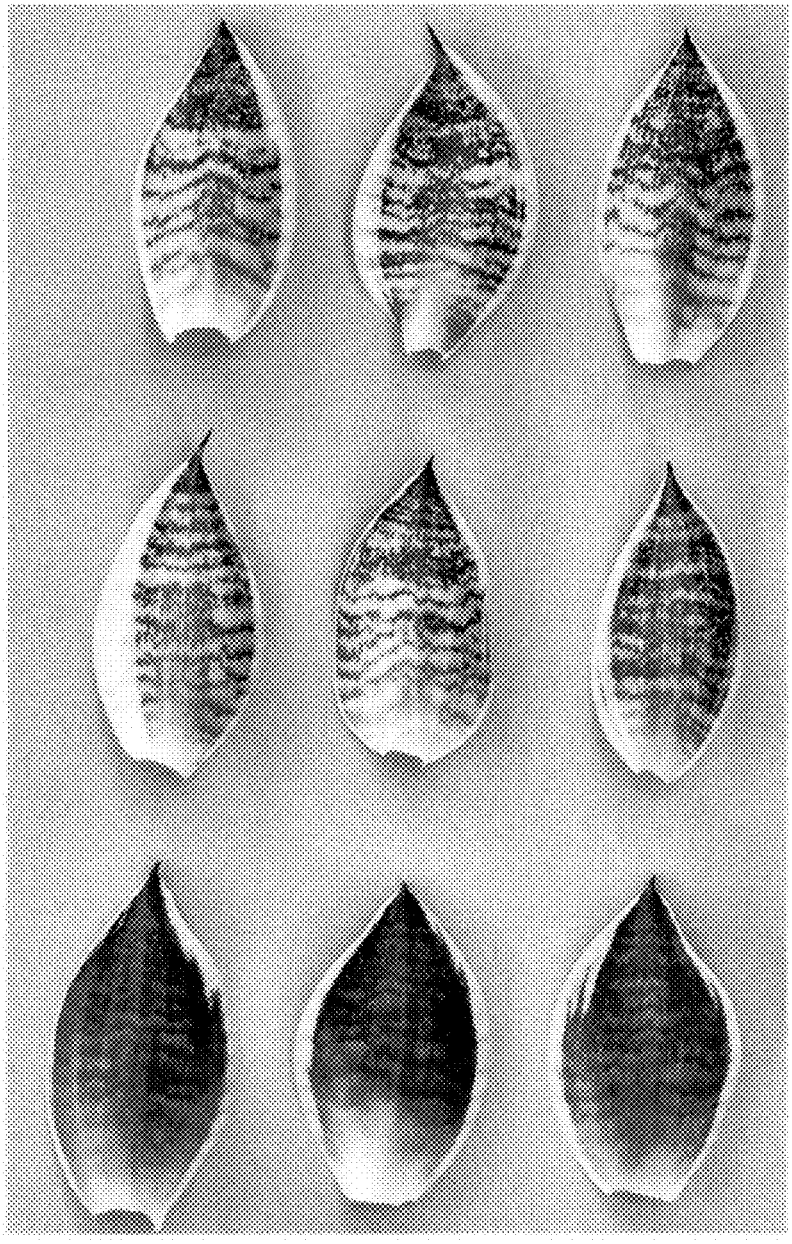

FIG. 7 is a comparison of the bottom surface foliage of the new cultivar, parent variety and a comparator cultivar. Bottom surface of individual leaves of *Sansevieria trifasciata* 'Hahnii Jade Marginata', parental variety (Top row) and leaves of the comparable variety *Sansevieria* 'Hansoti22' (Bottom row) leaves of the new variety, *Sansevieria trifasciata* 'Hansoti40' (Middle row).

DETAILED BOTANICAL DESCRIPTION

The new *Sansevieria* 'HANSOTI40' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI40' plants grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer of slow-release 13:11:11 Type 360-days release at 1 kilo/cubic meter of media, Constant Liquid Feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (2001) except where general colors of ordinary significance are used.

The photographs and descriptions were taken during the monsoon season in Asle, District Satara, Maharashtra State, India when outdoor day temperature was 25° C. to 30° C. The age of the plants described is 3-4 months.

Botanical classification: *Sansevieria trifasciata* 'HANSOTI40'.

General information:

*Parentage*.—*Sansevieria trifasciata* 'Hahnii Jade Marginata' (unpatented).

*Optimal growth conditions*.—

*Light intensities*.—High adaptability to outdoor or indoor conditions, but needs some shade in hot climates. Shade levels of 35% to 75% depending on season to give maximum light intensity of 350 to 500 μmol/m2/s.

*Temperature*.—Day: 25° C. to 35° C. Night: 15° C. to 25° C.

*Temperature tolerance*.—Tolerant to a low temperature of about 6° C. and a high temperature of 39° C. and above — very heat tolerant.

*Fertilization*.—Constant feed of 100 ppm N, 20 ppm P and 100 ppm K is used along with micronutrients with occasional leaching. Slow-release fertilizer 13:11:11 added at 1 kg/cubic meter of growing media.

*Growth regulators*.—Not necessary for growth, however rooting hormone aids in rapid and prolific rooting of offsets.

Propagation:

*Typical*.—Vegetative, by side suckers which come true to type. Does not come true from leaf cuttings.

*Rooting habit and description*.—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots*.—25 to 30 days at 25° C. to 30° C.

*Time to produce a rooted liner*.—About 45 days at 25° C. to 30° C.

*Time to produce ready* 12 *cm potted plant from liner*.—About 10 to 12 weeks at 25° C. to 30° C.

Plant:

*General appearance and form*.—Monocot; leaf bases arranged in a rosette around growth point.

*Height*.—About 14 to 16 cm when grown in 12 cm pots.

*Spread*.—About 18 to 22 cm when grown when grown in a 12 cm size container.

*Growth rate and habit*.—Moderate growth rate, stays flat and compact for a long time.

*Shape*.—Rosette.

*Fragrance*.—None.

*Stem*.—Modified (Rhizomes which are fleshy with erect foliage, branching and giving offsets so forming clumps in time).

*Rosette height*.—About 14-16 cm height above pot when grown in 12 cm size container.

*Rosette diameter*.—About 18 cm to 22 cm.

*Texture*.—Smooth, waxy.

*Strength*.—Strong and durable.

*Internode length*.—About 1 mm.

Foliage:

*Quantity*.—About 10 to 13 in ready to sell plant. Number slowly increases with age.

*Arrangement and attachment*.—Single, alternate; leaf bases arranged stiffly in a rosette around central growth point.

*Leaf length*.—About 11 to 13 cm, full mature leaf.

*Leaf width*.—About 5 to 7 cm, full mature leaf.

*Overall shape of leaf*.—Lanceolate.

*Apex shape*.—Acute, triangular and aristate, with soft tip.

*Base shape*.—Plane.

*Margin*.—Sharp, smooth.

*Texture*.—Upper Surface: smooth and waxy texture.

*Texture*.—Under Surface: smooth and waxy texture.

*Pubescence*.—None.

*Color of immature leaf*.—Upper Surface: Near RHS Green 139A, with border near Yellow 4B. Prominent transverse banding of Yellow 4B and central wide band with sporadic traverse banding of Green 139A and Yellow-Green N144C to N144D. Margin Yellow 4B.

*Color of immature leaf*.—Lower Surface: Much more prominent transverse banding with narrower dark bands of RHS Yellow-Green 147A and broader lighter bands of 145C. The 18 longitudinal band so prominent and characteristic on the top surface is much subdued but perceptible on the bottom surface. Margin Yellow 4B.

*Color of mature leaf*.—Upper Surface: Near RHS Green 139A, with cream border near Yellow 4B. Prominent transverse banding of Yellow 4B and central wide band with sporadic traverse banding of Green 139A and of Yellow-Green N144C to N144D.

*Margins*.—Near RHS Yellow 4B.

*Crossbanding*.—Typical crossbanding as seen in most *Sansevieria trifasciata* cultivars with colour near RHS Yellow-Green 145C.

*Color of mature leaf*.—Lower Surface: Much more prominent transverse banding with narrower dark bands of RHS Yellow-Green 147A and broader lighter bands of 145C. The longitudinal band so prominent and characteristic on the top surface is much subdued but perceptible on the bottom surface.

*Margin*.—Near RHS Yellow 4B.

*Venation*.—Pattern: Longitudinal/parallel leaf shape.

*Venation color*.—Indistinguishable from leaf blade.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pets include *Pseudococcidae longispinus* and *Tetranychus urticae*.

*Disease resistance*.—Occasionally shows Anthracnose and leaf spots but largely disease free from clean mother stock.

*Fruit/seed production*.—No fruits/seeds detected to date.

What is claimed is:

1. A new and distinct cultivar of *Sansevieria* plant named 'HANSOTI40' as herein illustrated and described.

* * * * *